(12) United States Patent
Brannon

(10) Patent No.: US 9,566,053 B2
(45) Date of Patent: Feb. 14, 2017

(54) CANNULA POSITIONED TARGETING GUIDE

(71) Applicant: James K Brannon, Leawood, KS (US)

(72) Inventor: James K Brannon, Leawood, KS (US)

( * ) Notice: Subject to any disclaimer, the term of this patent is extended or adjusted under 35 U.S.C. 154(b) by 737 days.

(21) Appl. No.: 13/844,652

(22) Filed: Mar. 15, 2013

(65) Prior Publication Data

US 2013/0211200 A1    Aug. 15, 2013

Related U.S. Application Data

(63) Continuation-in-part of application No. 12/961,487, filed on Dec. 6, 2010, now abandoned.

(60) Provisional application No. 61/266,908, filed on Dec. 4, 2009.

(51) Int. Cl.

| A61M 5/178 | (2006.01) |
|---|---|
| A61B 1/00 | (2006.01) |
| A61B 1/04 | (2006.01) |
| A61B 17/02 | (2006.01) |
| A61B 1/018 | (2006.01) |
| A61B 17/34 | (2006.01) |
| A61B 17/00 | (2006.01) |

(52) U.S. Cl.
CPC ....... *A61B 17/0218* (2013.01); *A61B 1/00128* (2013.01); *A61B 1/018* (2013.01); *A61B 17/3403* (2013.01); *A61B 17/3421* (2013.01); *A61B 2017/00477* (2013.01); *A61B 2017/3411* (2013.01)

(58) Field of Classification Search
USPC ................ 600/102, 104, 106, 107, 114, 115, 600/121–125, 417, 429; 604/164.01–164.13, 166.01, 604/165.01–165.04, 174–186, 158, 604/170.02; 606/87, 96, 130
See application file for complete search history.

(56) References Cited

U.S. PATENT DOCUMENTS

| 2008/0262430 A1* | 10/2008 | Anderson et al. .......... 604/164.1 |
| 2010/0137681 A1* | 6/2010 | Ewers et al. .................. 600/102 |
| 2013/0030442 A1* | 1/2013 | Pilgeram ............ A61B 17/1764 606/96 |
| 2014/0336581 A1* | 11/2014 | Collin ....................... 604/164.05 |

OTHER PUBLICATIONS

U.S. Appl. No. 61/325,102, filed Apr. 16, 2010, James K. Brannon.
U.S. Appl. No. 12/763,213, filed Apr. 20, 2010, James K. Brannon.
U.S. Appl. No. 12/820,133, filed Jun. 21, 2010, James K. Brannon.

(Continued)

*Primary Examiner* — Ryan Henderson
(74) *Attorney, Agent, or Firm* — Intellectual Property Center, LLC; Arthur K. Shaffer

(57) ABSTRACT

The present invention provides a combination cannula positioned targeting guide adapted for angular receipt and support of a surgical instrument, the combination including an endoscopic portal having an enlarged membrane chamber having a rear port and an elongated portal cannula extending towards a portal tip, the rear port and the portal cannula being axially aligned; a portal stand extending from a substantially rectangular body towards an arcuate channel in communication with the enlarged membrane chamber; and the endoscopic portal being rotationally secured to the portal stand.

6 Claims, 3 Drawing Sheets

(56) References Cited

OTHER PUBLICATIONS

U.S. Appl. No. 12/908,879, filed Oct. 21, 2010, James K. Brannon.
U.S. Appl. No. 12/961,487, filed Dec. 6, 2010, James K. Brannon.
U.S. Appl. No. 12/961,491, filed Dec. 6, 2010, James K. Brannon.
U.S. Appl. No. 12/986,064, filed Jan. 6, 2011, James K. Brannon.
U.S. Appl. No. 61/443,655, filed Feb. 16, 2011, James K. Brannon.
U.S. Appl. No. 61/444,025, filed Feb. 17, 2011, James K. Brannon.
U.S. Appl. No. 61/444,315, filed Feb. 18, 2011, James K. Brannon.
U.S. Appl. No. 61/645,327, filed May 23, 2012, James K. Brannon.
U.S. Appl. No. 29/398,708, filed Aug. 3, 2011, James K. Brannon.
U.S. Appl. No. 13/444,559, filed Apr. 11, 2012, James K. Brannon.
U.S. Appl. No. 13/039,191, filed Mar. 2, 2011, James K. Brannon.
U.S. Appl. No. 13/076,408, filed Mar. 30, 2011, James K. Brannon.
U.S. Appl. No. 13/089,306, filed Apr. 18, 2011, James K. Brannon.
U.S. Appl. No. 13/197,476, filed Aug. 3, 2011, James K. Brannon.
U.S. Appl. No. 29/445,846, filed Feb. 18, 2013, James K. Brannon.
U.S. Appl. No. 10/928,553, filed Aug. 26, 2004, James Kevin Brannon.
U.S. Appl. No. 11/970,246, filed Jan. 7, 2008, James K. Brannon.
U.S. Appl. No. 12/369,388, filed Feb. 11, 2009, James K. Brannon.
U.S. Appl. No. 12/181,205, filed Jul. 28, 2008, James K. Brannon.
U.S. Appl. No. 12/369,575, filed Feb. 11, 2009, James K. Brannon.
U.S. Appl. No. 12/706,706, filed Feb. 6, 2010, James K. Brannon.
U.S. Appl. No. 13/361,823, filed Jan. 30, 2012, James K. Brannon.
U.S. Appl. No. 61/170,508, filed Apr. 17, 2009, James K. Brannon.
U.S. Appl. No. 61/253,068, filed Oct. 20, 2009, James K. Brannon.
U.S. Appl. No. 61/218,757, filed Jun. 19, 2009, James K. Brannon.
U.S. Appl. No. 29/340,631, filed Jul. 22, 2009, James K. Brannon.
U.S. Appl. No. 61/266,908, filed Dec. 4, 2009, James K. Brannon.
U.S. Appl. No. 61/266,900, filed Dec. 4, 2009, James K. Brannon.
U.S. Appl. No. 61/303,496, filed Feb. 11, 2010, James K. Brannon.
U.S. Appl. No. 61/303,508, filed Feb. 11, 2010, James K. Brannon.
U.S. Appl. No. 61/309,732, filed Mar. 2, 2010, James K. Brannon.
U.S. Appl. No. 61/319,166, filed Mar. 30, 2010, James K. Brannon.
U.S. Appl. No. 61/325,084, filed Apr. 16, 2010, James K. Brannon.

* cited by examiner

CANNULA POSITIONED TARGETING GUIDE

CROSS-REFERENCE TO RELATED APPLICATION

This application claims the benefit of the prior filed U.S. non-provisional application Ser. No. 12/961,487 filed on Dec. 6, 2010 which claimed the benefit of prior filed U.S. provisional application No. 61/266,908 filed Dec. 4, 2009 which are incorporated herein by reference.

FIELD OF THE INVENTION

The present invention is broadly directed to improvements in instruments for endoscopic surgery and, more particularly, to a combination cannula positioned targeting guide for facilitating alignment of a received surgical instrument with an axis of the surgical portal to thereby assist in angular alignment of and to limit undesired lateral movement of the received instrument.

BACKGROUND OF THE INVENTION

Surgical portals allow for accessing underlying body tissue in order to introduce surgical objects during a medical procedure. Typically, surgical ports are used in minimally invasive procedures including arthroscopic, laparoscopic, an endoscopic procedures.

As minimally invasive surgeries involve making one or more small incisions at appropriate locations and inserting surgical instruments through the incisions to the surgical site, surgical portals allow for such surgical instruments to be more efficiently and safely used. Controlling the surgical instruments is of utmost importance as the surrounding tissue can easily be damaged through inadvertent contact with the instruments.

In many instances, the surgical portal is used to maintain a pathway from an external incision to a surgical site, such as a hip joint. The portal scope is of such a diameter that incorrect placement of the distal tip within the joint capsule could injure the femoral head or other organs or tissues of other types of endoscopic surgical sites. Therefore, accurate placement is very desirable. In some situations, it is desirable for the surgical portal to be transparent to enable viewing through a surgical instrument with a viewing scope to observe the environment of the surgical site.

SUMMARY OF THE INVENTION

The present invention provides improvements in surgical instrumentation by providing a combination cannula positioned targeting guide adapted for angular receipt and support of a surgical instrument, the combination comprising an endoscopic portal having an elongated portal cannula and a proximately positioned enlarged membrane chamber extending between a rearwardly positioned rear port and said elongated portal cannula; said rear port and said portal cannula being axially aligned; a longitudinal guide extending outwardly from an enlarged membrane chamber towards a portal cannula tip; a portal stand extending from a substantially rectangular body towards an arcuate channel in communication with said enlarged membrane chamber and received by said rear port; said endoscopic portal being rotationally keyed to said portal stand; and said portal stand including an angular passageway presenting an angular axis extending from said portal stand for intersection of said longitudinal guide extending outwardly from said elongated portal cannula.

Various objects and advantages of the present invention will become apparent from the following description taken in conjunction with the accompanying drawings and claims wherein are set forth, by way of illustration and example, certain embodiments of this invention.

The drawings constitute a part of this specification, include exemplary embodiments of the present invention, and illustrate various objects and features thereof.

DETAILED DESCRIPTION OF THE INVENTION

Figure 1:
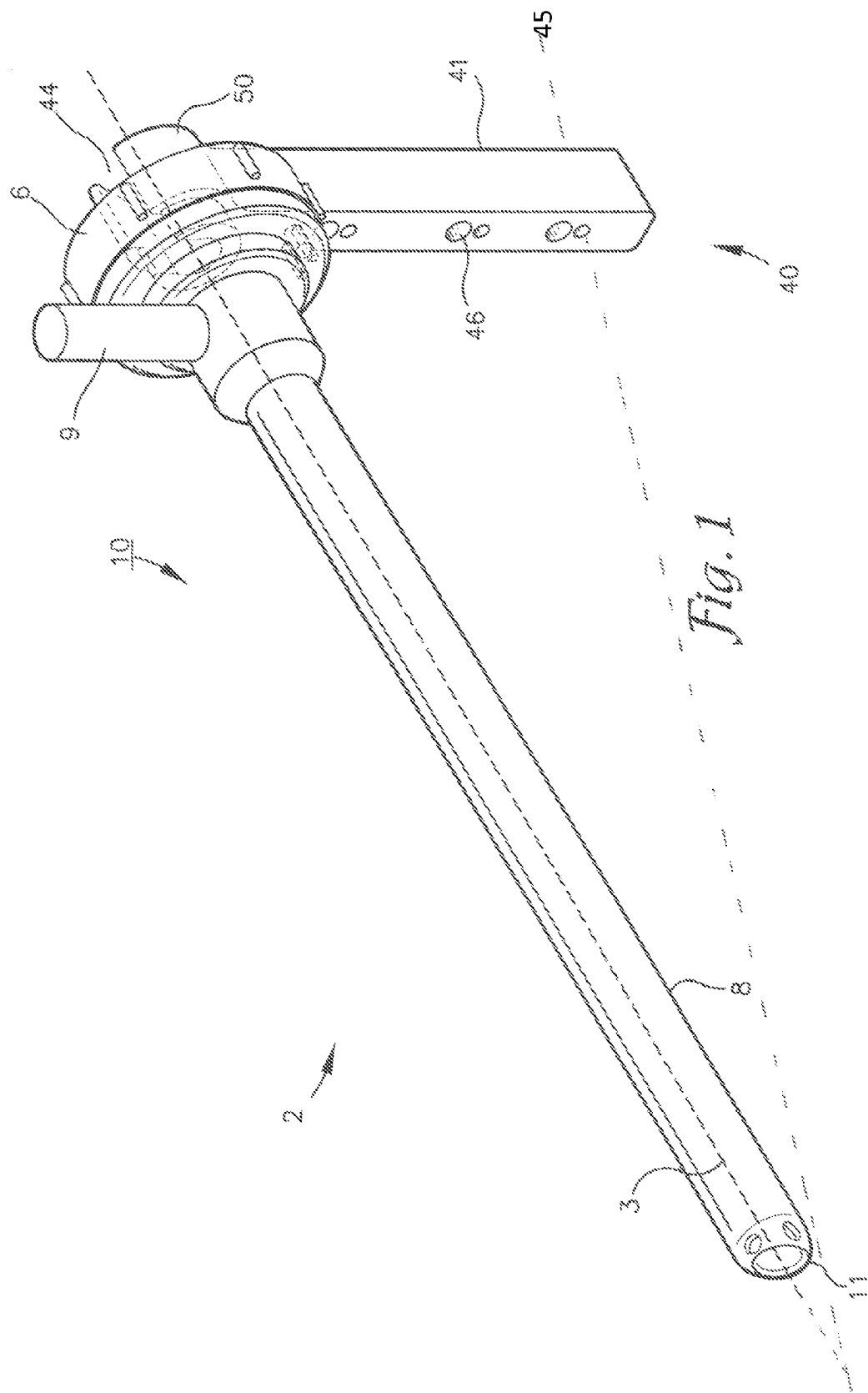
FIG. 1 is a side perspective of an embodiment of the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 (FIGS. 1-3) generally designates an embodiment of the combination cannula positioned targeting guide 10 for providing a plurality of alignment axes for the three-dimensional alignment of a surgical instrument (not shown) along a first longitudinal axis 3 associated with a portal scope 2 and at least a one angular axis 45 associated with an angled passageway associated with a portal stand 40, the portal being supported and in fixed rotational and angular orientation with respect to the angular axis 45.

In an embodiment, the portal stand 40 is rotationally fixed about the longitudinal axis 3 in a secured manner with an engaging key 42 associated with the portal stand 40 and a ribbed keyway 21 associated with the portal scope 2. As illustrated more clearly in FIG. 2, the key 43 extends outwardly from the portal stand 40 and the ribbed keyway 21 associated with the portal scope 2 includes a pair of substantially parallel ribs 22 spaced circumferentially along the enlarged membrane chamber 5.

Referring to FIG. 1, the illustrated assembly 10 includes the portal scope 2 engaged by the portal stand 40 which is vertically positioned with the sideport 9 in the upright position. The portal stand 40 is in communication with the portal scope for transmission of a surgical instrument, such as, but not limited to a trephine instrument or trephine (not shown) therethrough for passage along the elongated portal cannula towards a portal cannula tip 11.

Referring to FIG. 1, the illustrated portal scope 2 includes an enlarged membrane chamber 5. The membrane chamber 5 has a rear port (not shown) extending rearwardly therefrom and an elongated portal cannula 8 extending forwardly therefrom, the rear port and the portal cannula 8 being axially aligned. A side port 9 extends radially from the chamber 5 and is in communication with the chamber 5. A membrane 6 may be located within the enlarged membrane chamber 5, the membrane 6 having an opening for the receipt of the trephine or other surgical instrument. The rear port (not shown) of the enlarged membrane chamber 5 is adapted for receipt by the targeting device 40 and provides a barrier during a surgical procedure from contamination while providing an opening for receipt of the surgical instrument such as the trephine instrument, not shown. The side port 9 communicates directly with the portal cannula 8 through the distal side of the chamber, while the targeting device 40 is receivably engaged at the rear port (not shown). The portal cannula 8 terminates distally in a portal cannula tip 11. The illustrated tip 11 is conically tapered and cut off at an angle including at least one and as illustrated, a plurality of tip vents 12 located circumferentially along the tapered conical tip 11.

The enlarged membrane chamber 5 includes a rectangular toroid sidewall 5a having a rectangular cross section with an inner radius and an outer radius, the sidewall 5a extending from the rear port (not shown) and generally contiguous with an outer cylindrical chamber 13. As illustrated, the ribs 22 extend longitudinally and circumferential along the sidewall 5a. While the illustrated membrane chamber 5 is illustrated as being threaded, it may be formed utilizing a unitary or integrated molding process.

Figure 2:
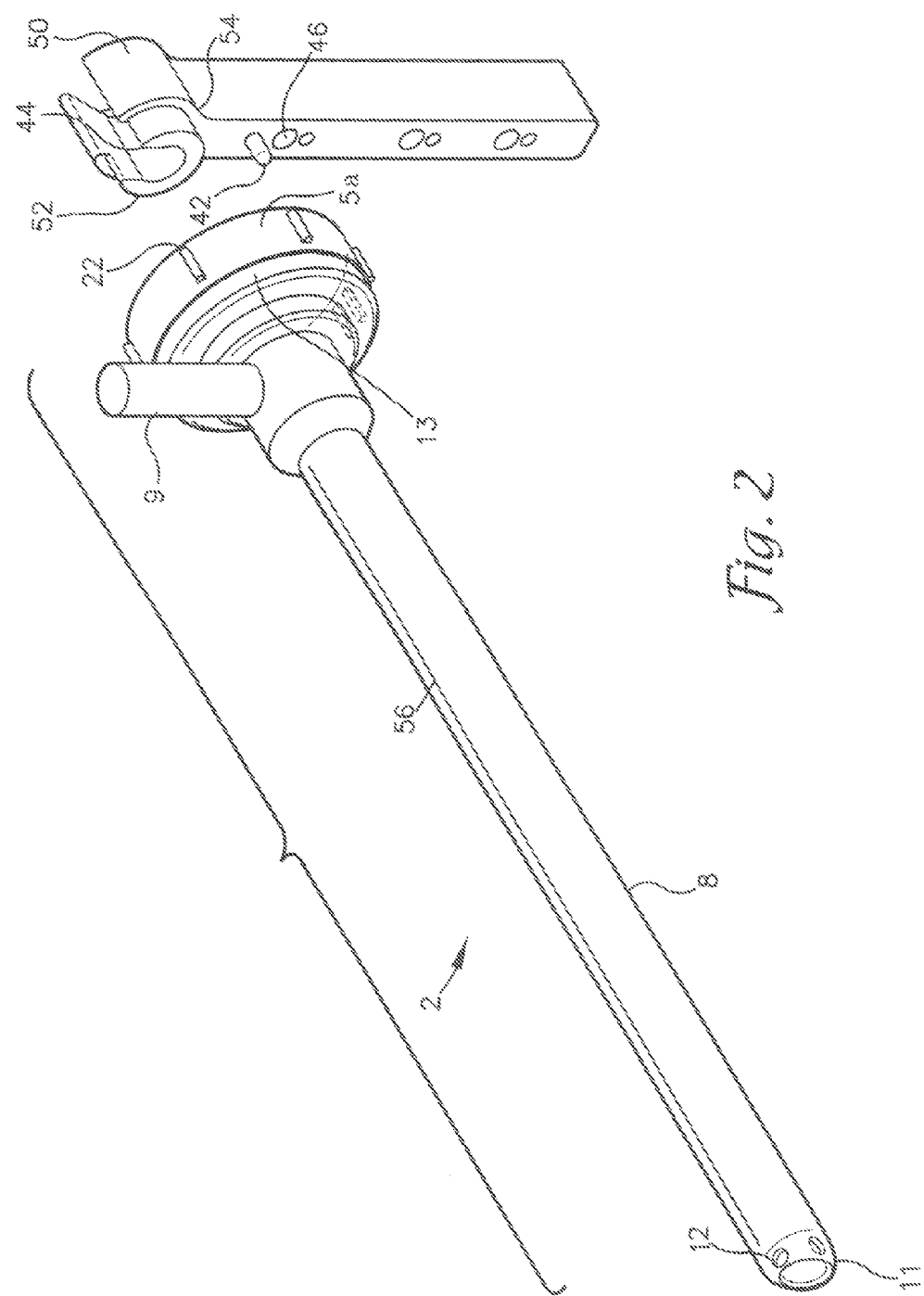
FIG. 2 is an exploded perspective view of the embodiment of FIG. 1.
Figure 3:
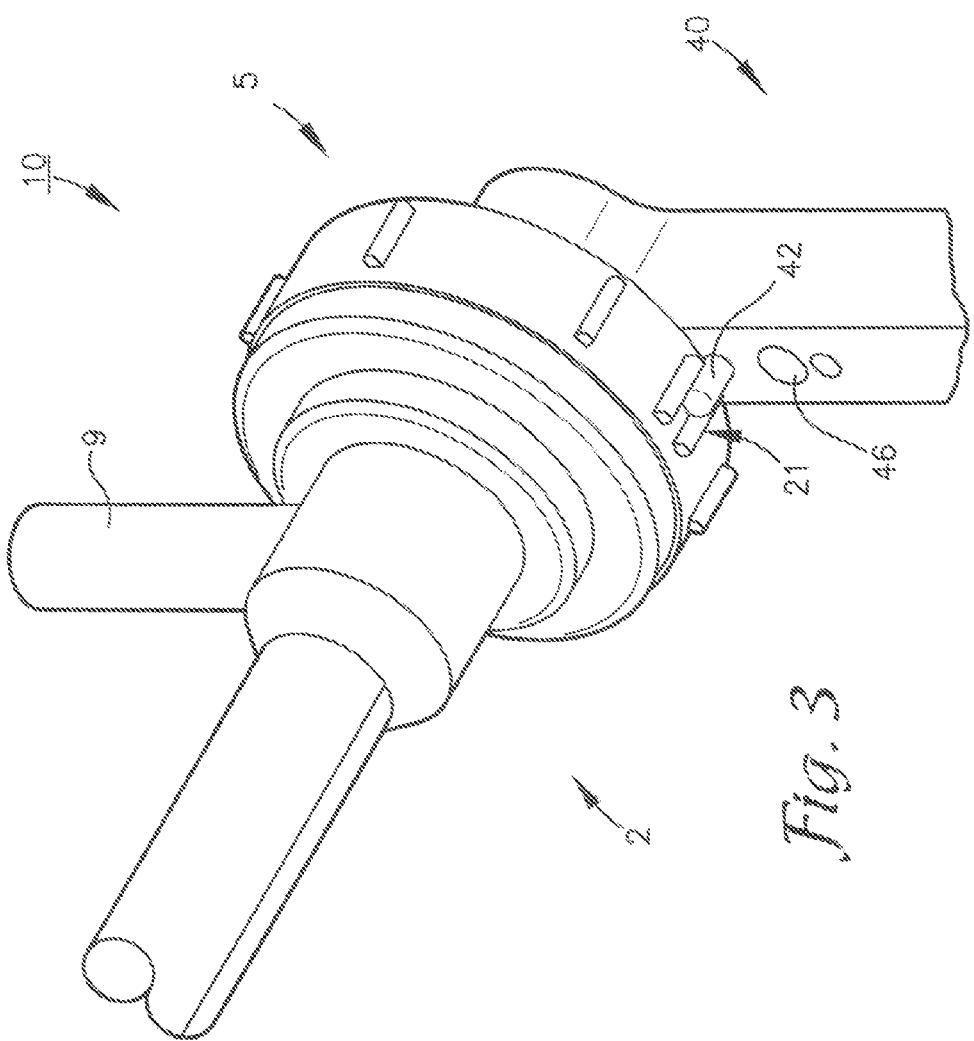
FIG. 3 is a fragmentary bottom perspective view of the embodiment of FIG. 1.

The portal stand 40 includes a substantially rectangular body 41 extending upwardly toward an arcuate channel 44 with an outer and inner crescent structure 50, 52. The arcuate channel 44 is adapted for circumferential receipt of a cylindrical shaft associated with a surgical instrument (not shown). In the exemplary embodiment, the outer crescent structure 50 extends from the substantially rectangular body 41 at an inflection point 54. The inner crescent structure 52 and outer crescent structure 50 present the contiguous arcuate channel 44. In FIGS. 1-3 the inner crescent 52 is illustrated as projecting outwardly from and radially discrete to the outer crescent structure 50. The outer crescent structure 50 provides the necessary support structure for supporting the portal scope 2 within the arcuate channel 44. During use, the inner crescent projection 52 is positioned at the rear port (not shown), the key 42 being aligned and placed into the ribbed keyway 21, the cylindrical instrument shaft (not shown) then being received by the arcuate channel 44 by passing the instrument shaft through the outer crescent projection 50 towards the inner crescent projection 52 and then into the elongated membrane chamber 5 down the elongated portal cannula 8 to the desired location. In addition, during use a longitudinal guide 56 projects a visual axis along the elongated cannula 8, providing a visual reference indication to assist in providing feedback for proper angled and positional orientation of the surgical instruments during use.

Generally, the portal stand 40 includes plural angular passageways 46 for angular alignment. Various surgical instruments may be passed through the desired angular passageways 46, each optionally presenting a different angled orientation. For example, the larger diameter passageways may be configured to represent 10 deg. increments while the smaller diameter passageways may be configured to represent 5 deg. increments, however, these are only exemplary illustrations and they could be configured or organized having a variety of angular orientations.

In another alternative embodiment, the cannula tip 11 includes a lens or prism element associated with the distal end of the tip 11. The lens may include a planar surface associated with the inner diameter of the cannula (not shown) which may be conically configured for presenting an angled lens surface.

Alternatively, the elongated cannula 8 may include a transparent surface with the longitudinal guide 56. As the user presses the outer cannula surface onto the surrounding surfaces, the transparent surface may act as a lens and magnify the surrounding objects. As desired, the user may extend the trephine instrument 3 axially towards the rear port, allowing for greater visualization of the surrounding areas through the transparent elongated surface which presents the desired refraction index for magnifying the surrounding objects. The cannula outer surface may be fabricated from a suitable optical plastic or resin material which are generally known to the art.

It is to be understood that while certain forms of the present invention have been illustrated and described herein, it is not to be limited to the specific forms or arrangement of parts described and shown.

What is claimed and desired to be secured by Letters Patent is:

1. A combination cannula positioned targeting guide adapted for angular receipt and support of a surgical instrument, the combination comprising:
    an endoscopic portal having a proximately positioned enlarged membrane chamber positioned thereat;
    said chamber having a rear port rearwardly extending therefrom and an elongated portal cannula extending forwardly from said chamber towards a portal cannula tip, the rear port and the portal cannula being axially aligned;
    a portal stand comprising a substantially rectangular body and an arcuate channel wherein said substantially rectangular body extends upwardly towards an arcuate channel and wherein said arcuate channel is in communication with said enlarged membrane chamber;
    an angled passageway disposed within said substantially rectangular body of the portal stand, wherein the angled passageway defines an angular axis that intersects a longitudinal axis of the portal cannula at the portal cannula tip;
    a longitudinal guide comprising a marking formed on the portal cannula extending from the enlarged membrane chamber to the portal cannula tip, wherein the longitudinal guide is aligned with the angular axis of said angled passageway;
    said arcuate channel extending proximally from said enlarged membrane chamber and coaxial with the longitudinal axis of the portal cannula when said endoscopic portal is rotationally keyed to said portal stand wherein an instrument is guided through said arcuate channel into said enlarged membrane chamber; and
    said endoscopic portal being rotationally secured to said portal stand.

2. The combination of claim 1 wherein said cannula is keyed to said portal stand.

3. The combination of claim 1 wherein said portal stand further includes a key and said endoscopic portal includes a ribbed passageway in receipt of said key.

4. The combination of claim 1 wherein said endoscopic portal includes a longitudinal guide presenting a visual reference along said endoscopic portal with said visual reference intersecting with said angular axis at said postal cannula tip.

5. The combination of claim 1 wherein said endoscopic portal is substantially transparent and includes a longitudinal guide presenting a visual reference extending from an outer cylindrical chamber to said portal cannula tip.

6. A combination cannula positioned targeting guide adapted for angular receipt and support of a surgical instrument, the combination comprising:
- an endoscopic portal having an elongated portal cannula and a proximately positioned enlarged membrane chamber extending between a rearwardly positioned rear port and said elongated portal cannula; said rear port and said portal cannula being axially aligned;
- a portal stand comprising a substantially rectangular body and an arcuate channel wherein said substantially rectangular body extends upwardly towards said arcuate channel and wherein said arcuate channel is in communication with said enlarged membrane chamber and received by said rear port;
- said endoscopic portal being rotationally keyed to said portal stand;
- said portal stand including an angular passageway presenting an angular axis extending from said portal stand for intersection of said longitudinal guide extending outwardly from said elongated portal cannula; and
- an angled passageway disposed within said substantially rectangular body of the portal stand, wherein the angled passageway defines an angular axis that intersects a longitudinal axis of the portal cannula at the portal cannula tip;
- a longitudinal guide comprising a marking formed on the portal cannula extending from the enlarged membrane chamber to the portal cannula tip, wherein the longitudinal guide is aligned with the angular axis of said angled passageway;
- said arcuate channel extending proximally from said enlarged membrane chamber and coaxial with the longitudinal axis of the portal cannula when said endoscopic portal is rotationally keyed to said portal stand wherein an instrument is guided through said arcuate channel into said enlarged membrane chamber.

* * * * *